US011298022B2

(12) United States Patent
Itoh et al.

(10) Patent No.: US 11,298,022 B2
(45) Date of Patent: *Apr. 12, 2022

(54) PROBE

(71) Applicant: TERUMO KABUSHIKI KAISHA, Tokyo (JP)

(72) Inventors: Ema Itoh, Kanagawa (JP); Kazuyuki Takahashi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 541 days.

This patent is subject to a terminal disclaimer.

(21) Appl. No.: 16/282,460

(22) Filed: Feb. 22, 2019

(65) Prior Publication Data

US 2019/0183341 A1    Jun. 20, 2019

Related U.S. Application Data

(63) Continuation of application No. 14/491,289, filed on Sep. 19, 2014, now Pat. No. 10,213,109, which is a
(Continued)

(30) Foreign Application Priority Data

Mar. 28, 2012    (JP) .................................. 2012-072863

(51) Int. Cl.
*A61B 5/00*    (2006.01)
*A61B 8/00*    (2006.01)
*A61B 8/12*    (2006.01)

(52) U.S. Cl.
CPC .......... *A61B 5/0035* (2013.01); *A61B 5/0066* (2013.01); *A61B 5/0084* (2013.01);
(Continued)

(58) Field of Classification Search
None
See application file for complete search history.

(56) References Cited

U.S. PATENT DOCUMENTS 5,876,344 A    3/1999    Baker
7,599,588 B2    10/2009    Eberle
(Continued)

FOREIGN PATENT DOCUMENTS

JP    11056752 A    3/1999
JP    2005095624 A    4/2005
(Continued)

OTHER PUBLICATIONS

International Search Report (PCT/ISA/210) dated May 7, 2013, by the Japanese Patent Office as the International Searching Authority for International Application No. PCT/JP2013/001865.
(Continued)

*Primary Examiner* — Jonathan Cwern
(74) *Attorney, Agent, or Firm* — Buchanan Ingersoll & Rooney PC

(57) ABSTRACT

A configuration is provided for firmly fixing a transmitting and receiving unit for IVUS and a transmitting and receiving unit for OCT in a probe of an imaging apparatus for diagnosis in which space saving is achieved. The probe includes a cylindrical housing in which an ultrasonic wave transmitting and receiving unit is arranged on a distal side and a light transmitting and receiving unit is arranged on a proximal side. The ultrasonic wave transmitting and receiving unit and the light transmitting and receiving unit being fixed to the cylindrical housing in a state where a base of the ultrasonic wave transmitting and receiving unit and a base portion of the ball lens of the light transmitting and receiving unit are embedded in an adhesive agent.

20 Claims, 5 Drawing Sheets

Related U.S. Application Data continuation of application No. PCT/JP2013/001865, filed on Mar. 19, 2013.

(52) U.S. Cl.
CPC ................ *A61B 8/12* (2013.01); *A61B 8/445* (2013.01); *A61B 8/4416* (2013.01); *A61B 8/4461* (2013.01)

(56) References Cited

U.S. PATENT DOCUMENTS

| | | | |
|---|---|---|---|
| 10,213,109 B2* | 2/2019 | Itoh | ........................ A61B 8/445 |
| 2005/0101859 A1 | 5/2005 | Maschke | |
| 2005/0288582 A1 | 12/2005 | Yu et al. | |
| 2007/0173919 A1 | 7/2007 | Maschke | |
| 2009/0043191 A1 | 2/2009 | Castella | |
| 2009/0299195 A1 | 12/2009 | Muller et al. | |

FOREIGN PATENT DOCUMENTS

| | | |
|---|---|---|
| JP | 2006280449 A | 10/2006 |
| JP | 2009183416 A | 8/2009 |
| JP | 2010508973 A | 3/2010 |
| JP | 2011519689 A | 7/2011 |
| WO | 2008057573 A2 | 5/2008 |
| WO | 2009009802 A1 | 1/2009 |
| WO | 2009137659 A1 | 11/2009 |

OTHER PUBLICATIONS

J. Li et al., "Miniature integrated optical coherence tomography (OCT)-ultrasound (US) probe for intravascular imaging", Photonic Therapeutics and Diagnostics VIII, Feb. 3, 2012, pp. 1-7, vol. 8207, No. 1, XP060022630.

The extended European Search Report dated Oct. 29, 2015, by the European Patent Office in corresponding European Application No. 13768950.1 (8 pages).

* cited by examiner

PROBE

CROSS-REFERENCES TO RELATED APPLICATIONS

This application is a continuation of U.S. patent application Ser. No. 14/491,289 filed on Sep. 19, 2014, now U.S. Pat. No. 10,213,109, which is a continuation of International Application No. PCT/JP2013/001865 filed on Mar. 19, 2013, and claims priority to Japanese Application No. 2012-072863 filed on Mar. 28, 2012, the entire content of all three of which is incorporated herein by reference.

TECHNICAL FIELD

The disclosure here generally relates to a probe which is inserted into a body lumen when generating a tomographic image by using an imaging apparatus for diagnosis.

BACKGROUND DISCUSSION

Imaging apparatuses for diagnosis have been widely used to perform diagnoses of arteriosclerosis, and preoperative diagnoses during intra-vascular treatment using a high-performance catheter such as a balloon catheter or a stent, or to check postoperative results.

The imaging apparatus for diagnosis includes an intra-vascular ultra sound diagnostic apparatus (IVUS) and an optical coherence tomography apparatus (OCT) and the like, each of which has characteristics different from each other.

Recently, an imaging apparatus for diagnosis has been proposed in which the function of the IVUS and the function of the OCT are combined (for example, refer to Japanese Patent Application Publication No. 11-56752 and Japanese Patent Application Publication No. 2010-508973). In the imaging apparatus for diagnosis, a transmitting and receiving unit for IVUS and a transmitting and receiving unit for OCT are disposed in a distal end portion of an imaging core which is interpolated into a probe, and two types of tomographic images can be generated by using an ultrasonic wave and light which are respectively transmitted and received in the transmitting and receiving units.

In other words, when the imaging apparatus for diagnosis is used, it is possible to generate a tomographic image taking an advantage of the characteristics of the IVUS which can measure up to a high depth region and an advantage of the characteristics of the OCT which can measure an area in high resolution.

SUMMARY

However, space saving is indispensable when accommodating a transmitting and receiving unit for IVUS and a transmitting and receiving unit for OCT in a distal end portion of an imaging core. It is because the diagnostic target of an imaging apparatus for diagnosis is the inside of an extremely thin body lumen such as a blood vessel so that it is desirable for the diameter of the imaging core which is interpolated into a probe to be minimized as much as possible.

The probe disclosed here has been made taking the aforementioned problems into consideration, and aims to provide a configuration for fixing the transmitting and receiving unit for IVUS and the transmitting and receiving unit for OCT in the probe of the imaging apparatus for diagnosis in which space saving is achieved.

The probe includes a cylindrical housing in which an ultrasonic wave transmitting and receiving unit to transmit and receive an ultrasonic wave and a light transmitting and receiving unit to transmit and receive light are arranged. The probe transfers a signal to an imaging apparatus for diagnosis generating an ultrasonic wave tomographic image and a light tomographic image based on the signal obtained by transmitting and receiving the ultrasonic wave and the light in a state where the housing rotates to move inside a body lumen in an axial direction. An opening portion for the ultrasonic wave transmitting and receiving unit and the light transmitting and receiving unit to transmit and receive the ultrasonic wave and the light is provided on an upper side in the cylindrical surface of the housing. The ultrasonic wave transmitting and receiving unit is arranged on a distal side in the axial direction and the light transmitting and receiving unit is arranged on a proximal side in the axial direction respectively in the housing. Two signal wires of which one of the ends are connected to the ultrasonic wave transmitting and receiving unit and which extend to the outside of the housing toward the proximal side in the axial direction substantially parallel to each other are arranged in the housing so as to cause the distance between the two signal wires to be smaller than a width of an optical element configuring the light transmitting and receiving unit below the light transmitting and receiving unit.

According to the present disclosure, a transmitting and receiving unit for IVUS and a transmitting and receiving unit for OCT can be fixed to the probe of an imaging apparatus for diagnosis in which space saving is achieved.

In accordance with an aspect, a probe comprising: a cylindrical housing in which an ultrasonic wave transmitting and receiving unit to transmit and receive an ultrasonic wave, the ultrasonic wave transmitting and receiving unit including an oscillator, and a light transmitting and receiving unit to transmit and receive light are arranged, the light transmitting and receiving unit including an optical element, the optical element being a ball lens; at least two signal wires each having respective ends, the two signal wires being arranged in the cylindrical housing and extending to outside of the cylindrical housing toward a proximal side of the probe in an axial direction; the probe configured to transfer a signal to an operation control apparatus of an imaging apparatus for diagnosis, the operation control apparatus configured to generate an ultrasonic wave tomographic image and a light tomographic image based on the signal obtained by transmitting and receiving the ultrasonic wave and the light in a state where the cylindrical housing rotates to move inside a body lumen in the axial direction; an opening portion for the ultrasonic wave transmitting and receiving unit and the light transmitting and receiving unit to transmit and receive the ultrasonic wave and the light provided on an upper side of a cylindrical surface of the cylindrical housing; wherein the ultrasonic wave transmitting and receiving unit is arranged on a distal side of the cylindrical housing in the axial direction and the light transmitting and receiving unit is arranged on a proximal side of the cylindrical housing in the axial direction; the ultrasonic wave transmitting and receiving unit and the light transmitting and receiving unit being fixed to the cylindrical housing in a state where a base of the ultrasonic wave transmitting and receiving unit and a base portion of the ball lens of the light transmitting and receiving unit are embedded in an adhesive agent; and wherein the two signal wires connected to the oscillator of the ultrasonic wave transmitting and receiving unit and extending to the outside of the housing are embedded in the adhesive agent.

In accordance with another aspect, a probe comprising: a cylindrical housing in which an ultrasonic wave transmitting and receiving unit to transmit and receive an ultrasonic wave, the ultrasonic wave transmitting and receiving unit including an oscillator, and a light transmitting and receiving unit to transmit and receive light are arranged, the light transmitting and receiving unit including an optical element, the optical element being a ball lens; at least two signal wires each having respective ends, wherein a portion of each of the two signal wires overlaps the optical element in a direction parallel to a width the optical element; the probe being configured to transfer a signal to an operation control apparatus of an imaging apparatus for diagnosis, the operation control apparatus being configured to generate an ultrasonic wave tomographic image and a light tomographic image based on the signal obtained by transmitting and receiving the ultrasonic wave and the light in a state where the cylindrical housing rotates to move inside a body lumen in the axial direction; wherein an opening portion for the ultrasonic wave transmitting and receiving unit and the light transmitting and receiving unit to transmit and receive the ultrasonic wave and the light is provided on an upper side of a cylindrical surface of the cylindrical housing; wherein the ultrasonic wave transmitting and receiving unit is arranged on a distal side of the cylindrical housing in the axial direction and the light transmitting and receiving unit is arranged on a proximal side of the cylindrical housing in the axial direction; the ultrasonic wave transmitting and receiving unit and the light transmitting and receiving unit being fixed to the cylindrical housing in a state where a base of the ultrasonic wave transmitting and receiving unit and a base portion of the ball lens of the light transmitting and receiving unit are embedded in an adhesive agent; wherein the two signal wires connected to the oscillator of the ultrasonic wave transmitting and receiving unit and extending to the outside of the housing are embedded in the adhesive agent; and wherein at least one of the respective ends of each of the two signal wires is connected to the oscillator of the ultrasonic wave transmitting and receiving unit, and wherein the at least one of the respective ends of each of the two signal wires is not embedded in the adhesive agent.

In accordance with a further aspect, a probe comprising: a cylindrical housing in which an ultrasonic wave transmitting and receiving unit to transmit and receive an ultrasonic wave, the ultrasonic wave transmitting and receiving unit including an oscillator, and a light transmitting and receiving unit to transmit and receive light are arranged, the light transmitting and receiving unit including an optical element, the optical element being a ball lens; the cylindrical housing being partially filled with an adhesive agent, wherein the ultrasonic wave transmitting and receiving unit and the light transmitting and receiving unit are fixed to the cylindrical housing in a state where a base of the ultrasonic wave transmitting and receiving unit and at least a portion of the ball lens of the optical element are embedded in the adhesive agent; at least two signal wires each having respective ends, the two signal wires being embedded in the adhesive agent in the cylindrical housing and extending to outside of the cylindrical housing toward a proximal side of the probe in an axial direction; the probe being configured to transfer a signal to an operation control apparatus of an imaging apparatus for diagnosis, the operation control apparatus being configured to generate an ultrasonic wave tomographic image and a light tomographic image based on the signal obtained by transmitting and receiving the ultrasonic wave and the light in a state where the cylindrical housing rotates to move inside a body lumen in the axial direction; an opening portion for the ultrasonic wave transmitting and receiving unit and the light transmitting and receiving unit to transmit and receive the ultrasonic wave and the light provided on an upper side of a cylindrical surface of the cylindrical housing; the ultrasonic wave transmitting and receiving unit being arranged on a distal side of the cylindrical housing in the axial direction and the light transmitting and receiving unit being arranged on a proximal side of the cylindrical housing in the axial direction; and wherein at least one of the respective ends of each of the two signal wires is connected to the ultrasonic wave transmitting and receiving unit.

Other characteristics and advantages of the disclosure here will be obvious in the following description with reference to the accompanying drawings. Regarding the accompanying drawings, the same reference numerals and signs will be applied to the same or the similar configurations.

BRIEF DESCRIPTION OF THE DRAWINGS

The accompanying drawings are incorporated in this specification, take part in the configuration, and illustrate embodiments of the probe, thereby being used to explain the description and the principle of the probe disclosed here.

DETAILED DESCRIPTION

Hereinafter, each embodiment of the probe disclosed here will be described in detail with reference to the accompanying drawings.

First Embodiment

1. Configuration of Appearance of Imaging Apparatus for Diagnosis

Figure 1:
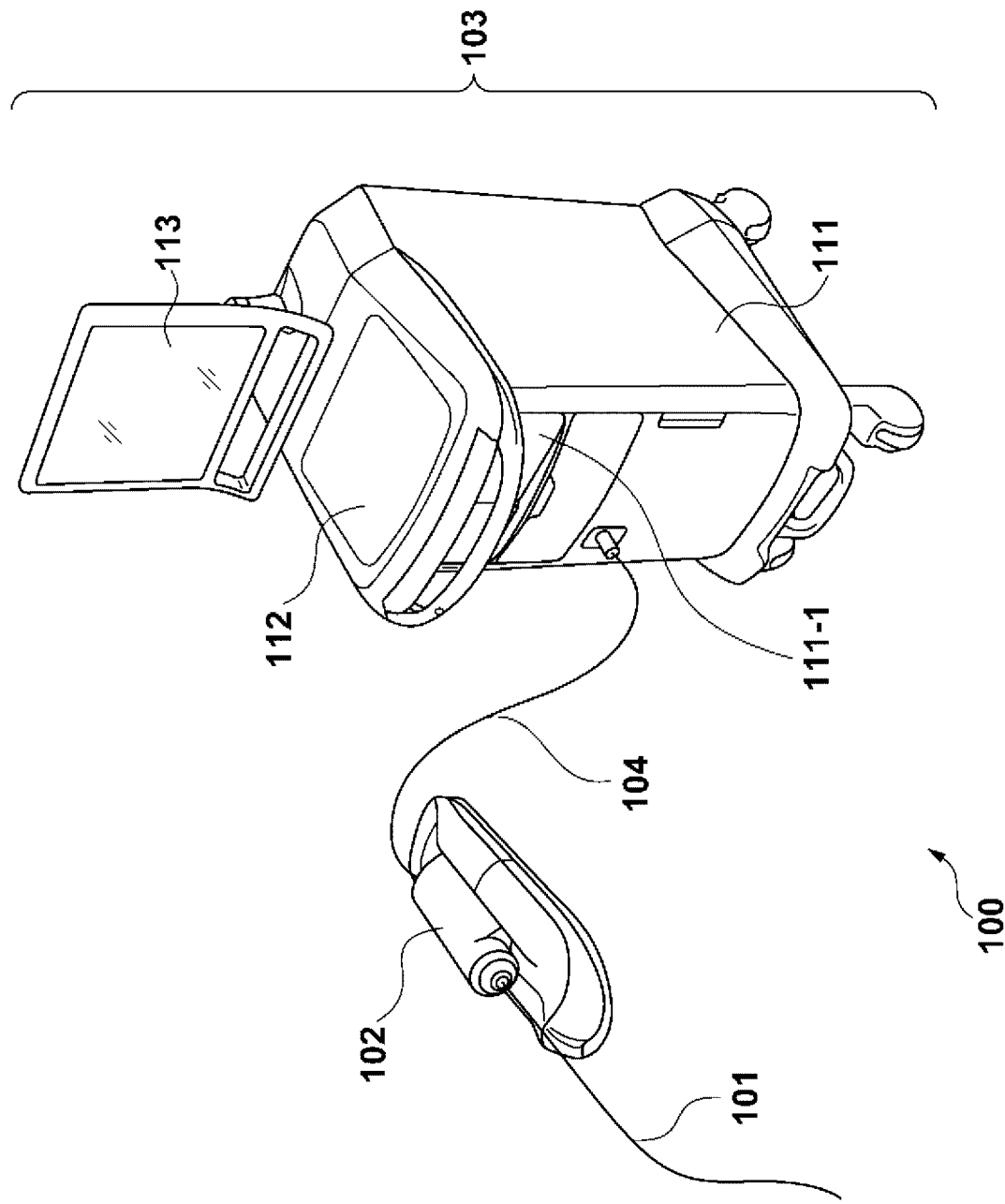
FIG. 1 is a view illustrating a configuration of an appearance of an imaging apparatus for diagnosis 100 according to an embodiment.

FIG. 1 is a view illustrating a configuration of an appearance of an imaging apparatus for diagnosis 100 (imaging apparatus for diagnosis provided with function of IVUS and function of OCT) according to an embodiment.

As illustrated in FIG. 1, the imaging apparatus for diagnosis 100 includes a probe unit 101, a scanner and pull-back unit 102 and an operation control apparatus 103. The scanner and pull-back unit 102 and the operation control apparatus 103 are connected to each other via a signal wire 104 which transfers various signals.

An imaging core which is directly inserted into a body lumen such as a blood vessel is interpolated into the probe unit 101. The imaging core includes an ultrasonic wave transmitting and receiving unit which transmits an ultrasonic wave based on a pulse signal to the inside of the body lumen and receives a reflected wave from a biological tissue inside the body lumen, and a light transmitting and receiving unit which continuously transmits transferred light (measurement light) to the inside of the body lumen and continuously receives reflected light from a biological tissue inside the body lumen. In the imaging apparatus for diagnosis 100, the imaging core is used to measure a state inside a body lumen.

The probe unit 101 is detachably attached to the scanner and pull-back unit 102 which regulates the imaging core interpolated into the probe unit 101 regarding an operation in an axial direction and an operation in a rotary direction inside a body lumen by driving a built-in motor. The scanner and pull-back unit 102 acquires the reflected wave received by the ultrasonic wave transmitting and receiving unit and the reflected light received by the light transmitting and receiving unit, thereby performing transmission to the operation control apparatus 103.

The operation control apparatus 103 includes a function for inputting various setting values when performing the measuring, and a function for processing data obtained through measurement and displaying it as a tomographic image inside a body lumen.

In the operation control apparatus 103, the reference numeral 111 indicates a main body control unit, which generates ultrasonic wave data based on a reflected wave obtained through the measurement, and processes line data generated based on the ultrasonic wave data, thereby generating an ultrasonic wave tomographic image. The main body control unit 111 generates interference light data by causing reflected light obtained through the measurement and reference light obtained by separating light from a light source to interfere with each other, and processes the line data generated based on the interference light data, thereby generating a light tomographic image.

The reference numeral 111-1 indicates a printer and a DVD recorder, which print a processing result of the main body control unit 111 or store the same as data. The reference numeral 112 indicates an operation panel, and a user inputs various setting values and instructions via the operation panel 112. The reference numeral 113 indicates an LCD monitor as a display device, which displays tomographic images (ultrasonic wave tomographic image and light tomographic image) generated in the main body control unit 111.

Figure 2:
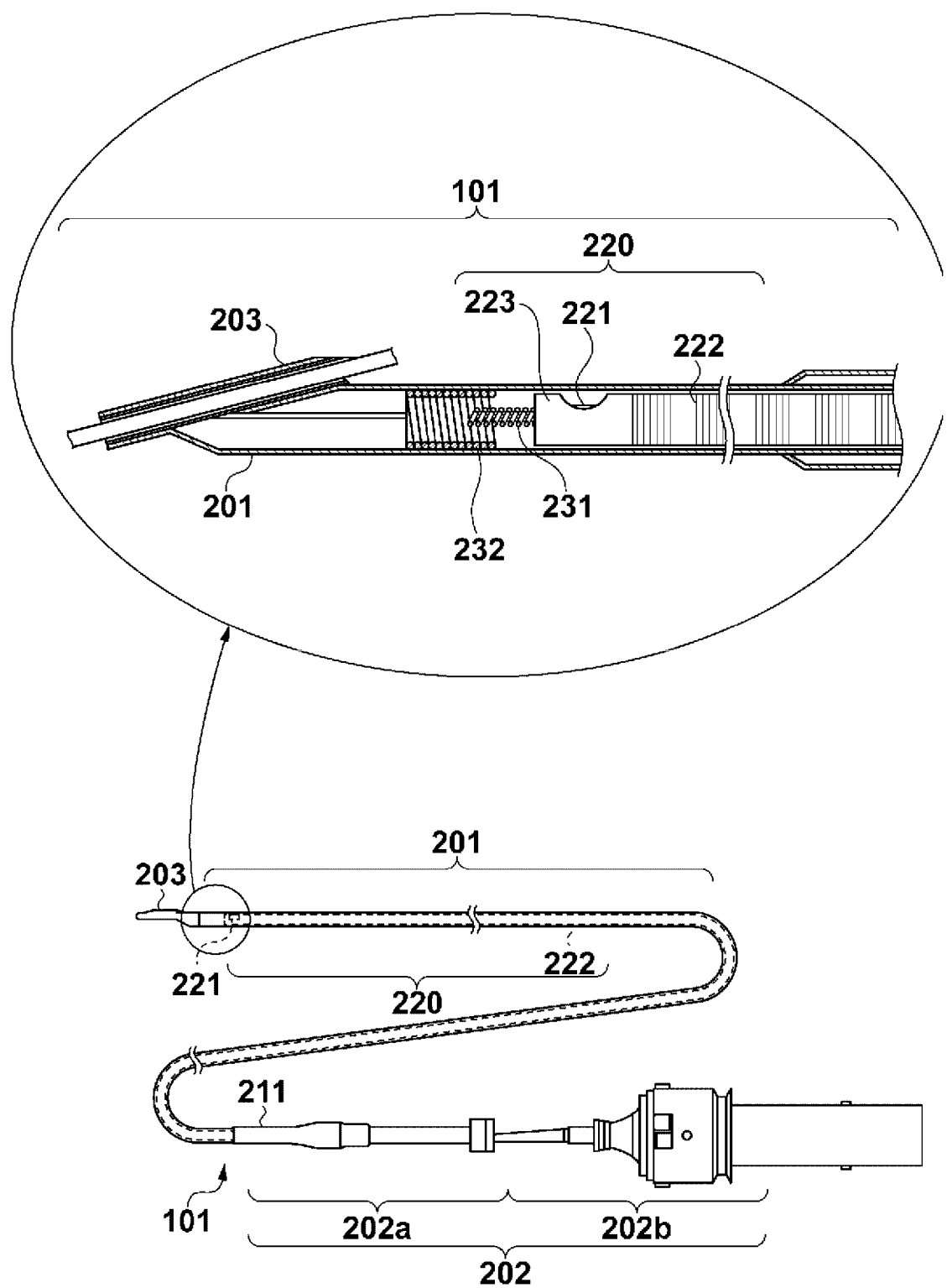
FIG. 2 is a view illustrating an overall configuration of a probe unit and a cross-sectional configuration of the distal end portion of the probe unit.

2. Overall Configuration of Probe Unit and Cross-Sectional Configuration of Distal End Portion of the Probe Unit Subsequently, an overall configuration of the probe unit 101 and a cross-sectional configuration of the distal end portion of the probe unit 101 will be described using FIG. 2. As illustrated in FIG. 2, the probe unit 101 is configured to include an elongated catheter sheath 201 which is directly inserted into a body lumen such as a blood vessel, and a connector unit 202 which is arranged on a hand side of a user to be manipulated by the user without being inserted into a body lumen such as a blood vessel. A tube for guide wire lumen 203 configuring a guide wire lumen is provided at a distal end of the catheter sheath 201. That is, the distal end of the catheter sheath 201 includes a tube 203 possessing a guide wire lumen configured to receive a guide wire. The catheter sheath 201 forms a lumen that continues from a portion connected to the tube for guide wire lumen 203 to a portion connected to the connector unit 202.

Inside a lumen of the catheter sheath 201, an imaging core 220 including a transmitting and receiving unit 221 and a coil-shaped drive shaft 222 is inserted through the catheter sheath 201 throughout substantially the overall length of the catheter sheath 201. The transmitting and receiving unit 221 includes the ultrasonic wave transmitting and receiving unit for transmitting and receiving an ultrasonic wave, and the light transmitting and receiving unit for transmitting and receiving light. The drive shaft 222 is internally provided with an electric signal cable and an optical fiber cable, and transfers a rotary drive force for rotating the transmitting and receiving unit 221.

The connector unit 202 includes a sheath connector 202a which is configured to be unified to a proximal end of the catheter sheath 201, and a drive shaft connector 202b which is configured to rotatably fix the drive shaft 222 at a proximal end of the drive shaft 222.

In a boundary portion between the sheath connector 202a and the catheter sheath 201, an anti-kink protector 211 is provided. Accordingly, a predetermined rigidity is maintained and bending (kink) due to a rapid change of physical properties can be prevented.

A proximal end of the drive shaft connector 202b is detachably attached to the scanner and pull-back unit 102.

Subsequently, a cross-sectional configuration of a distal end portion of the probe unit 101 will be described. As described above, inside a lumen of the catheter sheath 201, the imaging core 220 including the transmitting and receiving unit 221 and the drive shaft 222 is inserted through throughout substantially the overall length thereof, thereby forming the probe unit 101. The drive shaft 222 transfers a rotary drive force for rotating the transmitting and receiving unit 221 at a high speed.

The transmitting and receiving unit 221 transmits an ultrasonic wave and light toward a biological tissue inside a body lumen and receives a reflected wave and reflected light from a biological tissue inside a body lumen.

The drive shaft 222 has a coil shape and is provided with the electric signal cable and the optical fiber cable (single mode optical fiber cable).

The drive shaft 222 is configured to have a multiplex-multilayer bonding coil which can make the transmitting and receiving unit 221 to operate in a rotary direction and an axial direction with respect to the catheter sheath 201, and is made with a metal wire such as stainless steel having characteristics of being soft and favorably transferring rotations.

The housing 223 includes the transmitting and receiving unit 221 disposed therein. The housing 223 has a shape in which an opening portion is provided in a portion (upper side on cylindrical surface) of a short cylindrical metallic pipe. The housing 223 is molded through carving from matte, metal powder injection molding (MIM), and the like. The housing 223 internally houses the ultrasonic wave transmitting and receiving unit and the light transmitting and receiving unit as the transmitting and receiving unit 221. A proximal side of the housing 223 is connected to the drive shaft 222. A short coil-shaped elastic member 231 is provided on a distal side of the housing 223.

The elastic member 231 is a stainless steel wire having a coil shape, and the elastic member 231 is disposed on the distal side so as to prevent the imaging core 220 from being caught inside the catheter sheath 201 when the imaging core 220 moves back and forth.

A reinforcement coil 232 is provided for the purpose of preventing a sudden bending of a distal end portion of the catheter sheath 201.

The tube for guide wire lumen 203 has a lumen for a guide wire into which a guide wire can be inserted. The tube for guide wire lumen 203 receives a guide wire which is directly inserted into a body lumen such as a blood vessel, thereby being used for guiding the catheter sheath 201 to a target lesion through the guide wire.

3. Internal Configuration of Imaging Core

Figure 3A:
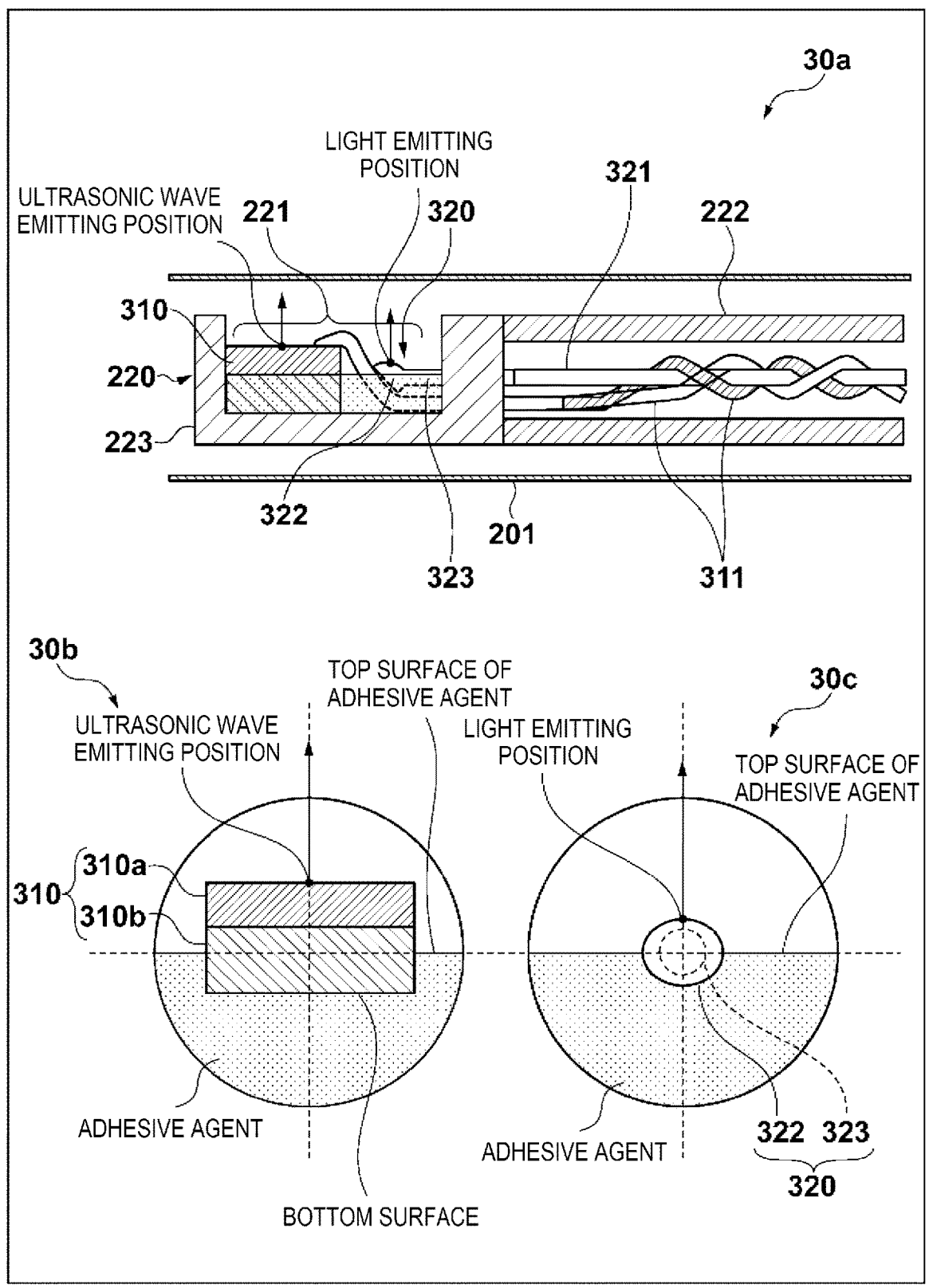
FIG. 3A is a view illustrating an arrangement of an ultrasonic wave transmitting and receiving unit and a light transmitting and receiving unit and an arrangement of cables in an imaging core.

Subsequently, an internal configuration of the imaging core 220 will be described in detail. FIG. 3A is a view for illustrating an arrangement of the ultrasonic wave transmitting and receiving unit and the light transmitting and receiving unit, and an arrangement of cables in the imaging core 220, in detail.

The drawing 30a of FIG. 3A illustrates a cross-sectional configuration when the imaging core 220 is seen from a side surface, and the drawings 30b and 30c of FIG. 3A illustrate cross-sectional configurations respectively in an ultrasonic emitting position and a light emitting position when the imaging core 220 is seen from the front (distal side). As illustrated in the drawing 30a of FIG. 3A, the transmitting and receiving unit 221 which is disposed inside the housing 223 in the distal end portion of the imaging core 220 includes an ultrasonic wave transmitting and receiving unit 310 and a light transmitting and receiving unit 320. The ultrasonic wave transmitting and receiving unit 310 and the light transmitting and receiving unit 320 are arranged inside the housing 223 along the axial direction. The ultrasonic wave transmitting and receiving unit 310 is arranged on the distal side of the imaging core 220, and the light transmitting and receiving unit 320 is arranged on the proximal side of the imaging core 220.

As illustrated in the drawings 30b and 30c of FIG. 3A, the cylindrical housing 223 is filled with an adhesive agent on the inner side of the cylindrical surface (in examples of 30b and 30c, inner side of the cylindrical surface on a lower side). Accordingly, inside the housing 223, the top surface of the adhesive agent is formed along the axial direction.

The ultrasonic wave transmitting and receiving unit 310 includes an oscillator 310a and a rear surface material 310b. The overall bottom surface of the rear surface material 310b is positioned on a lower side than the top surface of the adhesive agent (that is, the overall bottom surface of the rear surface material 310b is at least partially embedded in adhesive agent) so that the ultrasonic wave transmitting and receiving unit 310 is firmly fixed to the housing 223.

The light transmitting and receiving unit 320 is provided at the distal end of an optical fiber cable 321. The lower portion of a ball lens portion (optical element) 322 which has lens performance for collecting light and reflection performance for reflecting the same and the lower portion of a straight spacer portion 323 are positioned on lower sides than the top surface of the adhesive agent (that is, the lower portions of the ball lens portion 322 and the straight spacer portion 323 are at least partially embedded in adhesive agent). Accordingly, the light transmitting and receiving unit 320 is firmly fixed to the housing 223. A reflection surface of the ball lens portion 322 is formed by coating a reflection material onto an inclined surface of the ball lens portion 322.

As illustrated in 30a of FIG. 3A, one end of each of the two electric signal cables 311 for transmitting a pulse signal to the ultrasonic wave transmitting and receiving unit 310 and for transmitting a reflected wave which is received in the ultrasonic wave transmitting and receiving unit 310 to the operation control apparatus 103 is connected to the ultrasonic wave transmitting and receiving unit 310. The electric signal cables 311 extend to the drive shaft 222 (outside of housing 223) substantially parallel to each other via a path which does not interfere with the light emitting position of the light transmitting and receiving unit 320 inside the housing 223.

The electric signal cables 311 are disposed inside the drive shaft 222 while being wound around the optical fiber cable 321 of which one end is connected to the straight spacer portion 323 of the light transmitting and receiving unit 320 so as to form twisted wiring inside the drive shaft 222.

Figure 3B:
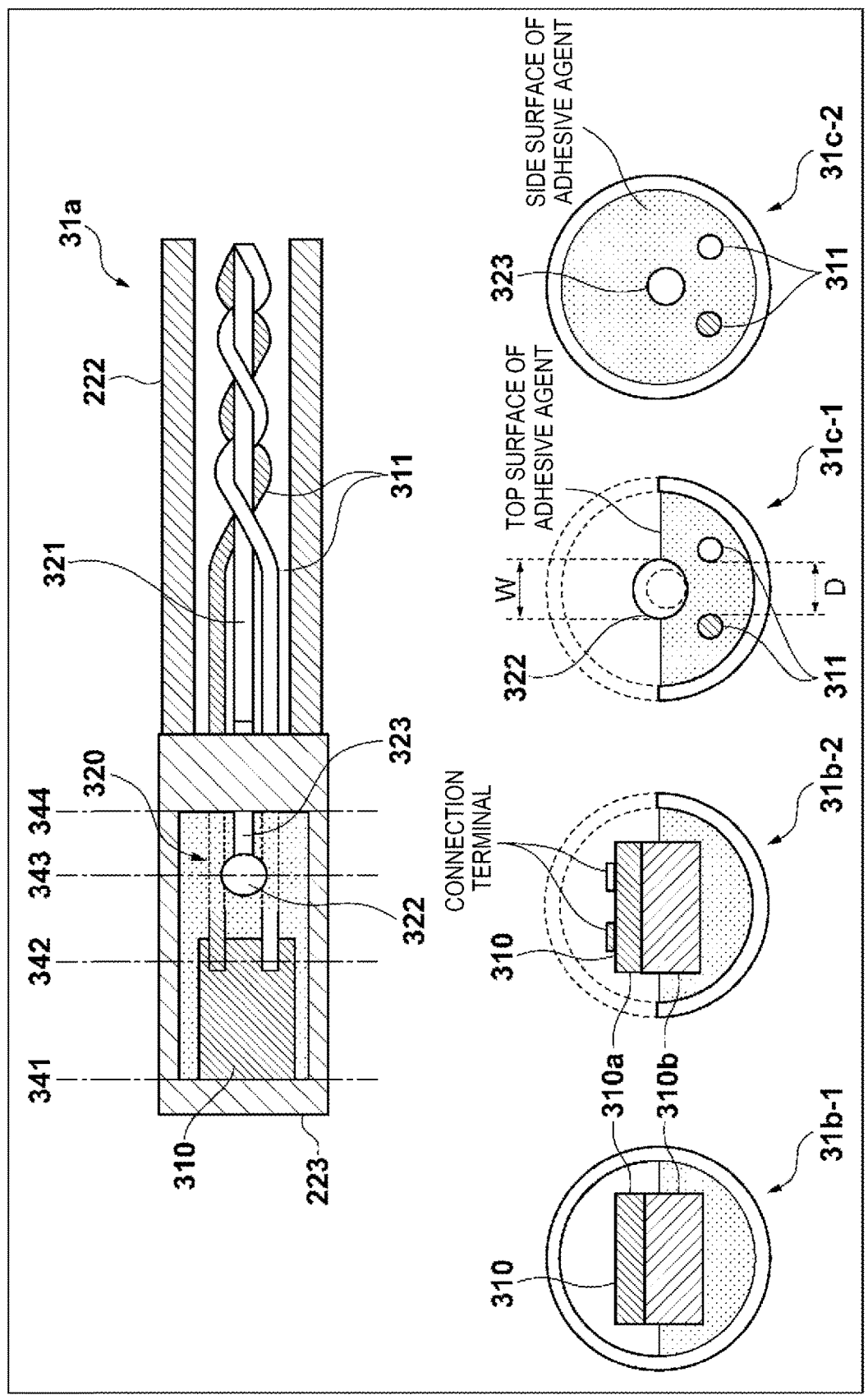
FIG. 3B is another view illustrating an arrangement of the ultrasonic wave transmitting and receiving unit and the light transmitting and receiving unit and an arrangement of the cables in the imaging core.

Subsequently, an internal configuration of the housing 223 will be described in detail using FIG. 3B. FIG. 3B is a view for illustrating an arrangement of the ultrasonic wave transmitting and receiving unit 310 and the light transmitting and receiving unit 320 and an arrangement of the cables in the housing 223.

The drawing 31a of FIG. 3B illustrates a planar configuration when the imaging core 220 is seen from the top surface, and the drawings 31b-1, 31b-2, 31c-1, and 31c-2 of FIG. 3B respectively illustrate cross-sectional configurations when seen from a distal side of the housing 223 having each of the positions of a plurality of dot and dash lines 341 to 344 indicated in the drawing 31a of FIG. 3B as the cut positions thereof.

As illustrated in the drawings 31a and 31c-1 of FIG. 3B, the two electric signal cables 311 connected to the ultrasonic wave transmitting and receiving unit 310 extend to the drive shaft 222 through a side lower than the top surface of the adhesive agent in the light emitting position (position indicated by dot and dash line 343) of the light transmitting and receiving unit 320 (that is, after being embedded in adhesive agent first in a light emitting position).

If the electric signal cables 311 connected to the ultrasonic wave transmitting and receiving unit 310 are stretched between connection terminals (refer to 31b-2) provided on the top surface of the oscillator 310a and a side surface of the adhesive agent (refer to 31c-2), and are arranged in a state of being hung in midair above the ball lens portion 322, when the imaging core 220 is made to rotate at a high speed, there is a possibility that the electric signal cables 311 may cause vibrations.

In contrast, as illustrated in the drawings 31a and 31c-1 of FIG. 3B, in the light emitting position, when the electric signal cables 311 are configured to pass at a portion lower than the top surface of the adhesive agent instead of a portion higher than the top surface of the adhesive agent, the electric signal cables 311 can avoid the state of being hung in midair inside the housing 223 so as to be firmly fixed to the housing 223. As a result, even when the imaging core 220 is made to rotate at a high speed, the electric signal cables 311 do not cause vibrations, and thus, it is possible to avoid influence on the measurement by the light transmitting and receiving unit 320.

As illustrated in the drawing 31c-1 of FIG. 3B, the two electric signal cables 311 connected to the ultrasonic wave transmitting and receiving unit 310 are arranged below the ball lens portion 322 configuring the light transmitting and receiving unit 320 so as to cause a distance D to be smaller than a width W of the ball lens portion 322. Accordingly, as illustrated in the drawing 31a of FIG. 3B, when the imaging core 220 is seen from the top surface, a portion of each of the two electric signal cables 311 overlaps with the ball lens portion 322. As a result, for example, compared to a case of being arranged on a side surface of the ball lens portion 322 (that is, compared to a case of being arranged without overlapping with the ball lens portion 322), the two electric signal cables 311 can be arranged in a space saving state.

As it is obvious from the above description, in the probe unit 101 according to the present embodiment, the ultrasonic wave transmitting and receiving unit 310 is arranged on the distal side of the probe unit 101 and the light transmitting and receiving unit 320 is arranged on the proximal side of the probe unit 101 inside the housing 223 which is provided in the distal end portion of the imaging core 220.

After filling the inside of the cylindrical surface on the lower side in the cylindrical surface forming the cylindrical housing 223 with the adhesive agent, the overall bottom surface of the rear surface material 310b of the ultrasonic wave transmitting and receiving unit 310 is arranged on a side lower than the top surface of the adhesive agent (that is, embedded into adhesive agent). Accordingly, the ultrasonic wave transmitting and receiving unit 310 could be firmly fixed to the housing 223.

Similarly, the lower portion of the ball lens portion 322 and the lower portion of a straight spacer portion 323 of the light transmitting and receiving unit 320 were configured to be embedded into the adhesive agent. Accordingly, the light transmitting and receiving unit 320 could be firmly fixed to the housing 223.

The electric signal cables 311 connected to the ultrasonic wave transmitting and receiving unit 310 were configured to be embedded in the adhesive agent in the light emitting position of the light transmitting and receiving unit 320. Accordingly, the electric signal cables 311 could avoid the state of being hung in midair inside the housing 223.

The electric signal cables 311 connected to the ultrasonic wave transmitting and receiving unit 310 were configured to be arranged at the distance D narrower than the width W of the ball lens portion 322 below the ball lens portion 322 configuring the light transmitting and receiving unit 320. Accordingly, the electric signal cables 311 could be arranged inside the housing 223 in a space saving state.

As a result, in the probe of the imaging apparatus for diagnosis, even when the imaging core rotates at a high speed, it is possible to securely suppress an occurrence of vibrations or the like and to minimize the diameter of the imaging core as much as possible.

Second Embodiment

In the first embodiment, according to the above-described configuration, in addition to the aspect in which the transmitting and receiving unit for IVUS and the transmitting and receiving unit for OCT can be firmly fixed to the housing 223, the description has also been made regarding the aspect regarding the arrangement in which space saving can be achieved. However, a space saving effect of the arrangement becomes remarkable when the diameter of the ball lens portion 322 is increased. That is, a space saving effect of the arrangement is enhanced when the diameter of the ball lens portion 322 is increased.

Hereinafter, a description will be given in detail regarding an aspect in which the space saving effect of the arrangement is enhanced when the diameter of the ball lens portion 322 is increased.

Figure 4:
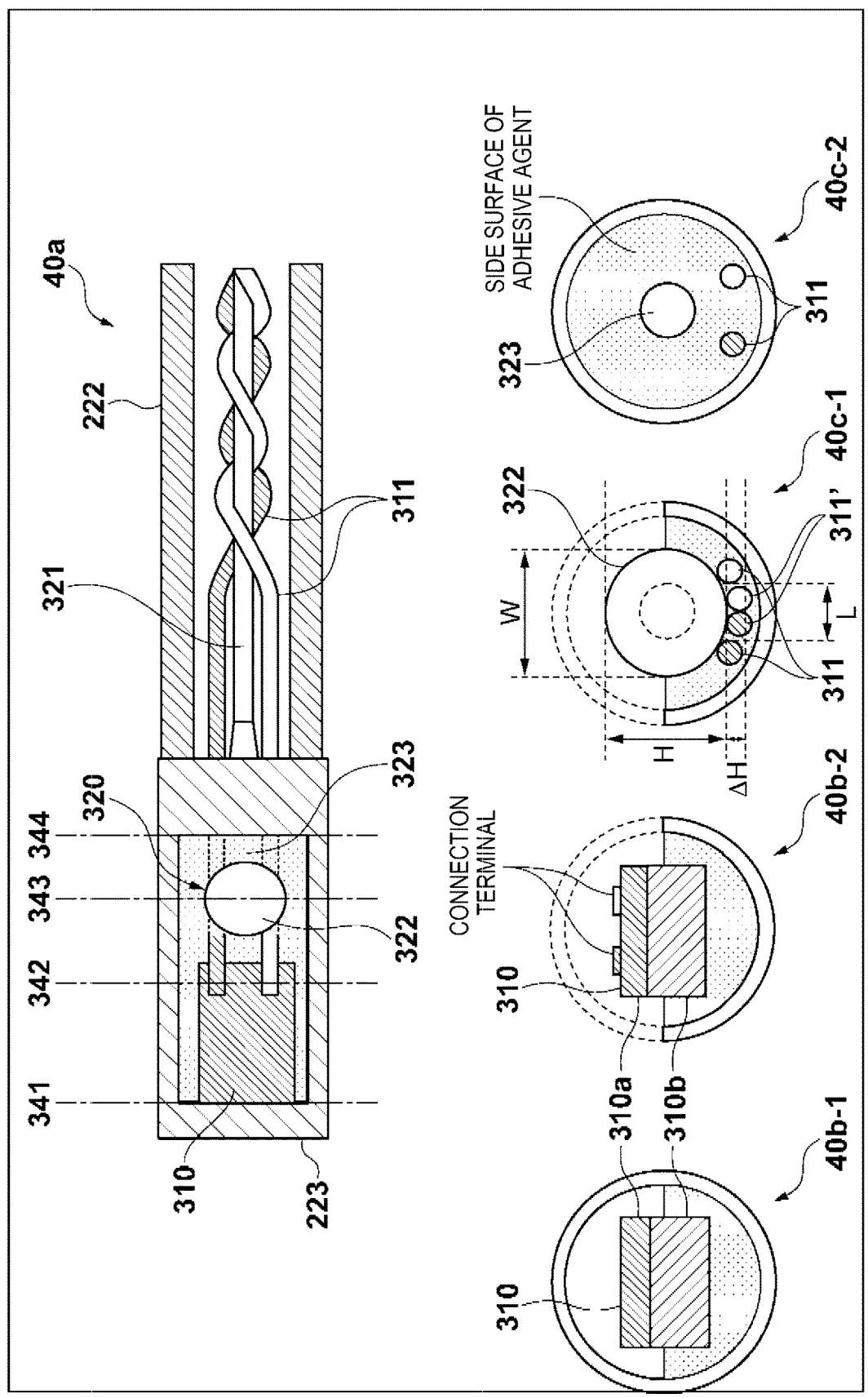
FIG. 4 is another view illustrating an arrangement of the ultrasonic wave transmitting and receiving unit and the light transmitting and receiving unit and an arrangement of the cables in the imaging core.

FIG. 4 is a view for illustrating an arrangement of the ultrasonic wave transmitting and receiving unit 310 and the light transmitting and receiving unit 320 and an arrangement of the cables in the housing 223 in detail. FIG. 4 differs from FIG. 3 in that the ball lens portion 322 and the straight spacer portion 323 have large diameters.

In this manner, when the diameter of the ball lens portion 322 is increased, if the electric signal cables 311 connected to the ultrasonic wave transmitting and receiving unit 310 are arranged so as to pass through the side surface of the ball lens portion 322, the diameter of the inner wall of the housing 223 needs to be greater than the sum of the diameter of the ball lens portion 322 and the diameters of the two electric signal cables 311.

In contrast, as illustrated in the drawings 40a and 40c-1 of FIG. 4, the electric signal cables 311 connected to the ultrasonic wave transmitting and receiving unit 310 can be accommodated within a range of the width W of the ball lens portion 322 by arranging the electric signal cables 311 in the light emitting position of the light transmitting and receiving unit 320 along the lower surface of the ball lens portion 322.

In this case, a projecting amount 4H of the electric signal cables 311 in a downward direction with respect to the height H of the ball lens portion 322 can be minimized by arranging the electric signal cables 311 to be separated by a predetermined distance L (compared to a case where the electric signal cables 311 are arranged side by side along the lower surface of the ball lens portion 322 (that is, L=0) (refer to the reference numeral 311' within dotted lines), the projecting amount ΔH of the electric signal cables 311 in the downward direction can be suppressed). Accordingly, the electric signal cables 311 can be accommodated inside the housing 223 in which space saving is further achieved.

In other words, even when the diameter of the ball lens portion 322 is increased, the diameter of the probe can be maintained.

In the first embodiment and the second embodiment described above, examples are described using a ball lens as an optical element. However, without being limited thereto, the probe disclosed here may be configured to use optical elements such as the ball lens, a gradient index-type (GRIN) lens, a reflection-type prism, and an aspheric lens.

The detailed description above describes embodiments of a probe and imaging apparatus representing examples of the probe and imaging apparatus of the present invention. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A probe comprising:
a cylindrical housing in which an ultrasonic wave transmitting and receiving unit to transmit and receive an ultrasonic wave, the ultrasonic wave transmitting and receiving unit including an oscillator, and a light transmitting and receiving unit to transmit and receive light are arranged, the light transmitting and receiving unit including an optical element, the optical element being a ball lens;
at least two signal wires each having respective ends, the two signal wires being arranged in the cylindrical housing and extending to outside of the cylindrical housing toward a proximal side of the probe in an axial direction;
the probe configured to transfer a signal to an operation control apparatus of an imaging apparatus for diagnosis, the operation control apparatus configured to generate an ultrasonic wave tomographic image and a light tomographic image based on the signal obtained by transmitting and receiving the ultrasonic wave and the light in a state where the cylindrical housing rotates to move inside a body lumen in the axial direction;
an opening portion for the ultrasonic wave transmitting and receiving unit and the light transmitting and receiving unit to transmit and receive the ultrasonic wave and the light provided on an upper side of a cylindrical surface of the cylindrical housing;
wherein the ultrasonic wave transmitting and receiving unit is arranged on a distal side of the cylindrical housing in the axial direction and the light transmitting and receiving unit is arranged on a proximal side of the cylindrical housing in the axial direction;
the ultrasonic wave transmitting and receiving unit and the light transmitting and receiving unit being fixed to the cylindrical housing in a state where a base of the ultrasonic wave transmitting and receiving unit and a base portion of the ball lens of the light transmitting and receiving unit are embedded in an adhesive agent; and
wherein the two signal wires connected to the oscillator of the ultrasonic wave transmitting and receiving unit and extending to the outside of the housing are embedded in the adhesive agent.

2. The probe according to claim 1, wherein a side of the cylindrical housing is filled with the adhesive agent, the adhesive agent having a cylindrical surface and a top surface formed along the axial direction.

3. The probe according to claim 2, wherein the two signal wires are disposed along a lower surface of the optical element of the light transmitting and receiving unit.

4. The probe according to claim 3, wherein the two signal wires are arranged so as to be accommodated within the width of the optical element of the light transmitting and receiving unit.

5. The probe according to claim 4, wherein the two signal wires are separated from each other by a predetermined distance on the lower surface of the optical element.

6. The probe according to claim 1, further comprising:
a drive shaft connected to the housing and transferring a rotary drive force for rotating the housing, and wherein the two signal wires are wound around an optical fiber which is connected to the light transmitting and receiving unit so as to form twisted wiring inside the drive shaft.

7. The probe according to claim 1, further comprising:
a reflection surface of the ball lens, wherein the reflection surface is a coating of a reflection material on an inclined surface of the ball lens.

8. The probe according to claim 1, wherein the ultrasonic wave transmitting and receiving unit further includes a base material, the base material being embedded in the adhesive agent; and
at least one of the respective ends of each of the two signal wires is connected to the oscillator of the ultrasonic wave transmitting and receiving unit, and wherein the at least one of the respective ends of each of the two signal wires is not embedded in the adhesive agent.

9. A probe comprising:
a cylindrical housing in which an ultrasonic wave transmitting and receiving unit to transmit and receive an ultrasonic wave, the ultrasonic wave transmitting and receiving unit including an oscillator, and a light transmitting and receiving unit to transmit and receive light are arranged, the light transmitting and receiving unit including an optical element, the optical element being a ball lens;
at least two signal wires each having respective ends, wherein a portion of each of the two signal wires overlaps the optical element in a direction parallel to a width the optical element;
the probe being configured to transfer a signal to an operation control apparatus of an imaging apparatus for diagnosis, the operation control apparatus being configured to generate an ultrasonic wave tomographic image and a light tomographic image based on the signal obtained by transmitting and receiving the ultrasonic wave and the light in a state where the cylindrical housing rotates to move inside a body lumen in the axial direction;
wherein an opening portion for the ultrasonic wave transmitting and receiving unit and the light transmitting and receiving unit to transmit and receive the ultrasonic wave and the light is provided on an upper side of a cylindrical surface of the cylindrical housing;
wherein the ultrasonic wave transmitting and receiving unit is arranged on a distal side of the cylindrical housing in the axial direction and the light transmitting and receiving unit is arranged on a proximal side of the cylindrical housing in the axial direction;
the ultrasonic wave transmitting and receiving unit and the light transmitting and receiving unit being fixed to the cylindrical housing in a state where a base of the ultrasonic wave transmitting and receiving unit and a base portion of the ball lens of the light transmitting and receiving unit are embedded in an adhesive agent;
wherein the two signal wires connected to the oscillator of the ultrasonic wave transmitting and receiving unit and extending to the outside of the housing are embedded in the adhesive agent; and
wherein at least one of the respective ends of each of the two signal wires is connected to the oscillator of the ultrasonic wave transmitting and receiving unit, and wherein the at least one of the respective ends of each of the two signal wires is not embedded in the adhesive agent.

10. The probe according to claim 9, wherein the two signal wires are arranged in the cylindrical housing so that a distance between the two signal wires is less than the width of the optical element.

11. The probe according to claim 9, wherein the optical element possesses an outer diameter, the outer diameter being the width of the optical element.

12. The probe according to claim 9, wherein a lower side of the cylindrical housing is filled with an adhesive agent.

13. The probe according to claim 9, further comprising:
a reflection surface of the ball lens, wherein the reflection surface is a coating of a reflection material on an inclined surface of the ball lens.

14. The probe according to claim 9, further comprising:
a drive shaft connected to the housing and transferring a rotary drive force for rotating the housing, and wherein the two signal wires are wound around an optical fiber which is connected to the light transmitting and receiving unit so as to form twisted wiring inside the drive shaft.

15. A probe comprising:
a cylindrical housing in which an ultrasonic wave transmitting and receiving unit to transmit and receive an ultrasonic wave, the ultrasonic wave transmitting and receiving unit including an oscillator, and a light transmitting and receiving unit to transmit and receive light are arranged, the light transmitting and receiving unit including an optical element, the optical element being a ball lens;
the cylindrical housing being partially filled with an adhesive agent, wherein the ultrasonic wave transmitting and receiving unit and the light transmitting and receiving unit are fixed to the cylindrical housing in a state where a base of the ultrasonic wave transmitting and receiving unit and at least a portion of the ball lens of the optical element are embedded in the adhesive agent;

at least two signal wires each having respective ends, the two signal wires being embedded in the adhesive agent in the cylindrical housing and extending to outside of the cylindrical housing toward a proximal side of the probe in an axial direction;

the probe being configured to transfer a signal to an operation control apparatus of an imaging apparatus for diagnosis, the operation control apparatus being configured to generate an ultrasonic wave tomographic image and a light tomographic image based on the signal obtained by transmitting and receiving the ultrasonic wave and the light in a state where the cylindrical housing rotates to move inside a body lumen in the axial direction;

an opening portion for the ultrasonic wave transmitting and receiving unit and the light transmitting and receiving unit to transmit and receive the ultrasonic wave and the light provided on an upper side of a cylindrical surface of the cylindrical housing;

the ultrasonic wave transmitting and receiving unit being arranged on a distal side of the cylindrical housing in the axial direction and the light transmitting and receiving unit being arranged on a proximal side of the cylindrical housing in the axial direction; and wherein at least one of the respective ends of each of the two signal wires is connected to the ultrasonic wave transmitting and receiving unit.

16. The probe according to claim 15, wherein the cylindrical housing possesses at least an axially extending part in which only a lower portion is filled with the adhesive agent.

17. The probe according to claim 15, wherein the ball lens of the optical element possesses an outer diameter, the outer diameter being the width of the optical element.

18. The probe according to claim 15, wherein a portion of each of the two signal wires overlaps the optical element in a direction parallel to the width of the optical element.

19. The probe according to claim 15, further comprising:
a reflection surface of the ball lens, wherein the reflection surface is a coating of a reflection material on an inclined surface of the ball lens.

20. The probe according to claim 15, further comprising:
a drive shaft connected to the housing and transferring a rotary drive force for rotating the housing, and wherein the two signal wires are wound around an optical fiber which is connected to the light transmitting and receiving unit so as to form twisted wiring inside the drive shaft.

* * * * *